US006821745B2

(12) United States Patent
Smith

(10) Patent No.: US 6,821,745 B2
(45) Date of Patent: Nov. 23, 2004

(54) REGULATION OF HUMAN PYROGLUTAMYL PEPTIDASE-LIKE ENZYME

(75) Inventor: Timothy J. Smith, Cambridge, MA (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/380,105

(22) PCT Filed: Sep. 5, 2001

(86) PCT No.: PCT/EP01/10206

§ 371 (c)(1), (2), (4) Date: Mar. 11, 2003

(87) PCT Pub. No.: WO02/22631

PCT Pub. Date: Mar. 21, 2002

(65) Prior Publication Data

US 2003/0176387 A1 Sep. 18, 2003

Related U.S. Application Data

(60) Provisional application No. 60/247,003, filed on Nov. 13, 2000, and provisional application No. 60/232,510, filed on Sep. 14, 2000.

(51) Int. Cl.[7] ............................ C12Q 1/37; C12N 9/64

(52) U.S. Cl. ........................................ 435/23; 435/226

(58) Field of Search .................................. 435/226, 23

(56) References Cited

U.S. PATENT DOCUMENTS 5,552,273 A 9/1996 Cleuziat et al.

FOREIGN PATENT DOCUMENTS

EP 0 911 411 7/1999

OTHER PUBLICATIONS

GenEMBL Data Base Acc#AB098134 Abe et al Nov. 8, 2003. Alignment with SEQ ID No.: 4.*

Abe et al Hydrolysis of synthetic substrate, L–pyroglutamyl p–nitroanilide is catalyzed solely by pyroglutamyl aminopeptidase I in rat liver cytosol. Biol Pharm Bull. Nov. 2003;26(11):1528–33.*

DatabaseEMBL "Online" Aug. 16, 2000, Dando et al "*Homo sapiens* mRNA for putative pyroglutamyl–peptidase–I (PGPEPI gene)" Database accesion No. AJ278828 (XP002199512).

DatabaseEMBL "Online" Aug. 16, 2000, Dando et al "*Homo sapiens* mRNA for putative pyroglutamyl–peptidase–I (PGPEPI gene)" Database accesion No. AJ278828 (XP002199512).

Cummins P M et al: "Pyroglutamyl peptidase: an overview of the three known enzymatic forms" Biochim. Biophys. Acta 1429, No. 1, Dec. 8, 1998, pp. 1–17 (XP004278561).

Schomberg L. et al.,; "Human TRH–degrading ectoenzyme, cDNA coloning, functional expression, genomic structure and chromosomal assignment" Eur. J. Biochem. vol. 265, 1999, pp. 415–422 (XP002199510).

Gonzales T and Robert–Baudouy J.: "Bacterial aminopeptidase: Properties and functions" Fems Microbiology Reviews vol. 18, 1996, pp. 319–344 (XP002199511).

Andrew Bateman et al. Post–translational modification of bovine pro–opiomelanocortin. Tyrosine sulfation and pyroglutamate formation, a mass spectrometric study, J Biol Chem Dec. 25, 1990; 265(36):22130–6.

John Pedersen et al. Removal of N–terminal polyhistidine tags from recombinant proteins using engineered aminopeptidases. Protein Expr Purif Apr.: 1999 15 (3): 389–400.

Gregor Czekay et al. Identification of the thyrotropin–releasing–hormone–degrading ectoenzyme as a metallopeptidase. Biochem J Mar. 15, 1993; 290 (Pt 3): 921–6.

Theodore C. Friedman et al. Delineation of a Particulate thyrotropin–releasing hormone–degrading enzyme in rat brain by the use of specific inhibitors of prolyl endopeptidase and pyroglutamyl peptide hydrolase. J Neurochem Apr. 1986; 46(4): 1231–9.

Charli. J.I., et al. TRH inactivation in the extracellular compartment role of pyroglutamyl peptidase II Neurobiology (Bp) 1998: 6 (1): 45–57.

* cited by examiner

*Primary Examiner*—Rebecca E. Prouty
*Assistant Examiner*—Sheridan Swope
(74) *Attorney, Agent, or Firm*—Banner & Witcoff, Ltd.

(57) ABSTRACT

Reagents which regulate human pyroglutamyl peptidase-like enzyme and reagents which bind to human pyroglutamyl peptidase-like enzyme gene products can play a role in preventing, ameliorating, or correcting dysfunctions or diseases, including, but not limited to, brain and spinal cord trauma, stroke, and neurodegenerative disorders, such as amyotropic lateral sclerosis and spinocerebellar degeneration.

3 Claims, 8 Drawing Sheets

Fig. 1 ttccaccatggagcagccgcggaaggcggtagtggtaaccggattcgg
ccctttggggagcatactgtgaatgccagctggatcgctgtccagga
gctggagaagctgggcctcggggacagcgtggacctgcatgtgtacga
gatccccgtggaataccagacggtgcagaggctcatcccagcactgtg
ggagaagcacagcccccagctcgtagtgcatgttggggtgtcgggcat
ggccaccacagtgacgctggaaaaatgtgggcacaacaagggttacaa
aggactggataattgccggttctgccccggctctcagtgctgcgtgga
ggatggtcccgagagcatcgactccatcatcgacatggacgccgtgtg
caaaagggtgaccacactgggactggacgtgtctgttaccatctccca
ggatgctggcaggtatctgtgtgacttcacgtattatacatcgctcta
ccagggccgcggccgctccgcttttgtccacgtgcccccactggtaag
ccctacaacgcc

Fig. 2 ttccaccatggagcagccgcggaaggcggtagtggtaaccggattcgg
ccctttggggagcatactgtgaatgccagctggatcgctgtccagga
gctggagaagctgggcctcggggacagcgtggacctgcatgtgtacga
gatccccgtggaataccagacggtgcagaggctcatcccagcactgtg
ggagaagcacagcccccagctcgtagtgcatgttggggtgtcgggcat
ggccaccacagtgacgctggaaaaatgtgggcacaacaagggttacaa
aggactggataattgccggttctgccccggctctcagtgctgcgtgga
ggatggtcccgagagcatcgactccatcatcgacatggacgccgtgtg
caaaagggtgaccacactgggactggacgtgtctgttaccatctccca
ggatgctggcaggtatctgtgtgacttcacgtattatacatcgctcta
ccagggccgcggccgctccgcttttgtccacgtgcccccactggtaag
ccctacaacgcc

Fig. 3 atggagcagccgaggaaggcggtggtagtgacgggatttggccc
ttttggggaacacaccgtgaacgccagttggattgcagttcagg
agctagaaaagctaggccttggcgacagcgtggacctgcatgtg
tacgagattccggttgagtaccaaacagtccagagactcatccc
cgccctgtgggagaagcacagtccacagctggtggtgcatgtgg
gggtgtcaggcatggcgaccacagtcacactggagaaatgtgga
cacaacaagggctacaaggggctggacaactgccgcttttgccc
cggctcccagtgctgcgtggaggacgggcctgaaagcattgact
ccatcatcgacatggatgctgtgtgcaagcgagtcaccacgttg
ggcctggatgtgtcggtgaccatctcgcaggatgccggcagata
tctctgcgactttacctactacacctctttgtaccagagtcacg
gtcgatcagccttcgtccacgtgcccccactggggaagccgtac
aacgcggaccagctgggcagggcactgagagccatcattgagga
gatgttggacctcctggagcagtcagagggcaaaatcaactatt
gccacaaacactga

Fig. 4

MEQPRKAVVVTGFGPFGEHTVNASWIAVQELEKLGLGDSVDLHVYEIP
VEYQTVQRLIPALWEKHSPQLVVHVGVSGMATTVTLEKCGHNKGYKGL
DNCRFCPGSQCCVEDGPESIDSIIDMDAVCKRVTTLGLDVSVTISQDA
GRYLCDFTYYTSLYQSHGRSAFVHVPPLGKPYNADQLGRALRAIIEEM
LDLLEQSEGKINYCHKH

Fig. 5

MRIVLLTGFEPFDQDPVNPSWEAVRQLDGVQLGSDVKIVARRLPCAFA
TAGECLTRLIDELHPAMVIATGLGPGRSDISVERVAININDARIPDNL
GEQPIDTAVVADGPAAFFTTLPIKAMVKAVREAGIAASVSQTAGTFVC
NQVFYLLQHALAGSGVRSGFIHVPFLPEQVAGSQRPSMALDAMVAGLQ
AAVLTAWHTPVDVKEAGGQVS

Fig. 6

MKVLVTGFEPFGGDKINPSWEAVKQLDGVREIGGATIVGRELPTSFKK
AAEVLKKAIAEIKPDIVIAIGLAPGRSAITVERVAINIDDAGRYGIPD
NEGEQPIDEPIVPDGPAAYFATLPVKAMVKAMREAGIPAAVSNTAGTF
VCNHVMYLLLHHSAKKGPPVRAGFIHVPYLPEQVVDKPNTGGKVVPSM
SLDTEVAGVTAAIEAALDYD

Fig. 7 agtcgcaacagaagcaggtccgaggcacagcccgatcccgccatggag
cagccgaggaaggcggtggtagtgacgggatttggccctttggggaa
cacaccgtgaacgccagttggattgcagttcaggagctagaaaagcta
ggccttggcgacagcgtggacctgcatgtgtacgagattccggttgag
taccaaacagtccagagactcatccccgccctgtgggagaagcacagt
ccacagctggtggtgcatgtgggggtgtcaggcatggcgaccacagtc
acactggagaaatgtggacacaacaagggctacaaggggctggacaac
tgccgctttgccccggctcccagtgctgcgtggaggacgggcctgaa
agcattgactccatcatcgacatggatgctgtgtgcaagcgagtcacc
acgttgggcctggatgtgtcggtgaccatctcgcaggatgccggcaga
tatctctgcgactttacctactacacctctttgtaccagagtcacggt
cgatcagccttcgtccacgtgcccccactggggaagccgtacaacgcg
gaccagctgggcagggcactgagagccatcattgaggagatgttggac
ctcctggagcagtcagagggcaaaatcaactattgccacaaacactga
gggacgctcaggtctcctaagacctcatcctgctggggaccccacgag
gggacatccaccctctggggtgtggccaggaaaagacaagctcttcag
cttggggatccgatctggaagagagattctgatctgcccacctcctct
tccttcttctctacaaaagctccggttgattcgagggaagtggtgaaa
atttttttttctcccatttcctccctgcatctggggacacagctgcc
gtgaccagggaggccagcctgggaggtccagatgcccagggagaatct
tggtctggtgaatccatgagctgagataccacggctggggccatatgt
tcacctgctttcctgtccgttggtgaaggaatttcagaattcatttta
tatccaagactggcttttaccaaatttaaaagcctctcaatgcgtcct
cgaccttgaactgtgctcaacagcctggccctttctggggccaccctg
ggatatggctggctggctggctggctttctttctttctttctttcttt
ctttctttctttctttctttctttctttctttcttgctttctttcttg
ctttctttcttgctttctttctttcttgctttctttcttctctctctc
tcttttttttttttttaaatagtgctagtttgggcacagagtaattta
tattccctttggttaaaatgcaggcttttagccaacaacaaaagtgt
tttccccccacccccactcgcccaccagggtgatgccacttttgcctc
ctgccctgaaaattggacttaagatgccatgtcttggctgggattaca
ggcatgagccactgcacccagcccagttctttcttaaaacagctgaga
gttttgttttcttcagcgttcaccttccttgtctccagttccgatgct
ggcagtggttcctacctctgttgggtttctagatagtttgggaacggg
gttgatgggtttctgtgaaacacattttccaagtcttgggctttctct
ggaggggaaggtggatgctggcgggtgacttgcagtgggcgcctggca
gtgggt

Figure 7 (continued)

gtggactgtaactgacaggtggaaatgagtaggggcactattgttccc
tccatgccagctttttttttgctggaaatgccccctccacaccccctgg
tagctctgtgtcctgagaaatccagagtgtgggagacatcactgcatc
tgtcccccccagcttctgtgaagggaagctgtggcctcttttgaatgtg
gggaacaactgaagactcaggggtcacccagaggtctggtggaaagca
acttcaggtttcatcttgctctattcctcaaaggtctggtctgtgggc
ctctgaggagaaaacaggtctagccaagacagggacaaaatggggaag
gggtgtgccaggcctgaactgagctaagcacctgccccgggctccac
acttccatctttcttttgtcttcatttcacctctgtgtttaaagcact
gtgtgacatagctccttagagatataacctattgtctgctcattgtca
aaaaaaaaaaaaaaaaaaaaaa

FIG. 8

BLASTP - alignment of SEQ ID NO:4 against aageneseq|R43316|R43316 (Accession No. P42673) (SEQ ID NO:5)

Pseudomonas fluorescens PYRase [PYRROLIDONE-CARBOXYLATE PEPTIDASE (EC 3.4.19.3) (5-OXOPROLYL-PEPTIDASE) (PYROGLUTAMYL-PEPTIDASE I) (PGP-I) (PYRASE)].
This hit is scoring at : 4e-15 (expectation value)
Alignment length (overlap) : 169
Identities : 28 %
Scoring matrix : BLOSUM62 (used to infer consensus pattern)
Database searched : aageneseq

```
Q:      6 KAVVVTGFGPFGEHTVNASWIAVQELEKLGLGDSVDLHVYEIPVEYQTVQRLIPALWEKH
          :.V::TGF PF.:..VN.SW AV::L: : LG..V.: . .:P..:.T. ..:..L ::
H:      2 RIVLLTGFEPFDQDPVNPSWEAVRQLDGVQLGSDVKIVARRLPCAFATAGECLTRLIDEL

          SPQLVVHVGVSGMATTVTLEKCGHNKGYKGL-DNCRFCPGSQCCVEDGPESIDSIIDMDA
          .P.:V: .G:.  .:.:::E:.. N . . : DN.  P ....V.DGP.:. :.:.:.A
          HPAMVIATGLGPGRSDISVERVAININDARIPDNLGEQPIDTAVVADGPAAFFTTLPIKA

          VCKRVTTLGLDVSVTISQDAGRYLCDFTYYT---SLYQSHGRSAFVHVP    170
          :.K.V...G  ::.::SQ.AG.::C: .:Y.   :L  S  RS.F:HVP
          MVKAVREAG--IAASVSQTAGTFVCNQVFYLLQHALAGSGVRSGFIHVP    168
```

The active-site residues, Glu85-Cys149-His168 (bold and underlined above), represent the catalytic triad of this peptidase.

FIG. 9

```
HMMPFAM - alignment of SEQ ID NO:4 against pfam|hmm|Peptidase_C15 (SEQ
ID NO:6)

Pyroglutamyl peptidase -

     This hit is scoring at : -44.5
     Scoring matrix : BLOSUM62 (used to infer consensus pattern)

Q:      6 KAVVVTGFGPFGEHTVNASWIAVQELEKLGLGDSVDLHVYEIPVEYQTVQRLIPALWEKH
            ..V:VTGF PFG ..:N.SW AV::L: :    ....:   E:P..:.:....:... .:
H:      1 mKVLVTGFePFGgdkiNPsweavkqLdGVreIggAtivgrelPtsFkkAaevLkkaiaei

          SPQLVVHVGVSGMATTVTLEKCGHNkgykgLDNC-R--------FCPGSQCCVEDGPESI
          .P.:V: :G::  .:.:T:E:.. N     :D:. R          P .: .V.DGP.:.
          kPDiVIaiGlAPGRsaITvERVAiN.....idDAGRYGIPDNeGeQPiDepIvpDGPaAY

          DSIIDMDAVCKRVTTLGldVSVTISQDAGRYLCDFTYYTSLYQS--HG---RSAFVHVPP
           :.:.:.A:.K.:...G  :...:S..AG.::C:...Y. L:.S  .G   R:.F:HVP
          FaTLPvKAMvkamreaG..iPAaVSntAGTFVCNhvmYlllhhsakkgppvraGFIHVPY

          L-----GKP-Y--------NADQLGRALRAIIEEMLDLL      196
          L     .KP          :.D.  ..:.A.IE..LD.
          lPeQVvdKpntgGkvvPSMsLdteVaGvtaAIeaAldyd  212
```

REGULATION OF HUMAN PYROGLUTAMYL PEPTIDASE-LIKE ENZYME

This application is a National Stage application of co-pending PCT application PCT/EP01/10206 filed Sep. 5, 2001, which was published in English under PCT Article 21(2) on Mar. 21, 2002, which claims the benefit of U.S. provisional application Ser. No. 60/232,510 filed Sep. 14, 2000 and Ser. No. 60/247,003 filed Nov. 13, 2000. These applications are incorporated herein by reference in their entireties.

TECHNICAL FIELD OF THE INVENTION

The invention relates to the area of enzyme regulation More particularly, the invention relates to the regulation of human pyroglutamyl peptidase I.

BACKGROUND OF THE INVENTION

The brain enzyme pyroglutamyl peptidase catalyzes the proteolysis of thyrotropin releasing hormone (TRH) to form histidyl-proline diketopiperazine, also known as cyclo (His-Pro) or CHP. U.S. Pat. No. 6,090,780. Because of the role of this enzyme in hormone metabolism, there is a need in the art to identify related enzymes which can be regulated to provide therapeutic effects.

SUMMARY OF THE INVENTION

It is an object of the invention to provide reagents and methods of regulating a human pyroglutamyl peptidase I This and other objects of the invention are provided by one or more of the embodiments described below.

One embodiment of the invention is a method of screening for agents which can regulate the activity of a human pyroglutamyl peptidase I. A test compound is contacted with a polypeptide comprising an amino acid sequence which is at least about 29% a identical to the amino acid sequence shown in SEQ ID NO:4. Binding of the test compound to the polypeptide is detected. A test compound which binds to the polypeptide is thereby identified as a potential therapeutic agent for regulating activity of the human pyroglutamyl peptidase I.

Another embodiment of the invention is a method of screening for agents which regulate an activity of a human pyroglutamyl peptidase I. A test compound is contacted with a polypeptide comprising an amino acid sequence which is at least about 29% identical to the amino acid sequence shown in SEQ ID NO:4. A pyroglutamyl peptidase I activity of the polypeptide is detected A test compound which decreases the pyroglutamyl peptidase I activity is thereby identified as a potential therapeutic agent for decreasing the activity of the human pyroglutamyl peptidase I. A test compound which increases the pyroglutamyl peptidase I activity of the polypeptide is thereby identified as a potential therapeutic agent for increasing the activity of the human pyroglutamyl peptidase I.

Yet another embodiment of the invention is a method of screening for agents which regulate an activity of a human pyroglutamyl peptidase I. A test compound is contacted with a product encoded by a polynucleotide which comprises a nucleotide sequence which is at least 50% identical to the nucleotide sequence shown in SEQ ID NO:3. Binding of the test compound to the product is detected A test compound which binds to the product is thereby identified as a potential therapeutic agent for regulating the activity of the human pyroglutamyl peptidase I.

Even another embodiment of the invention is a method of reducing activity of a human pyroglutamyl peptidase I. A cell is contacted with a reagent which specifically binds to a product encoded by a polynucleotide comprising a nucleotide sequence which is at least 50% identical to the nucleotide sequence shown in SEQ ID NO:3. The activity of the human pyroglutamyl peptidase I is thereby reduced Another embodiment of the invention is a pharmaceutical composition comprising a reagent which specifically binds to a product encoded by a polynucleotide comprising a nucleotide sequence which is at least 50% identical to the nucleotide sequence shown in SEQ ID NO:3 and a pharmaceutically acceptable carrier.

Another embodiment of the invention is a pharmaceutical composition comprising an expression construct encoding a polypeptide comprising the amino acid sequence shown in SEQ ID NO:4 and a pharmaceutically acceptable carrier.

Yet another embodiment of the invention is an isolated and purified polynucleotide consisting essentially of the nucleotide sequence shown in SEQ ID NO:3.

Still another embodiment of the invention is an isolated and purified polypeptide consisting essentially of the amino acid sequence shown in SEQ ID NO:4.

Even another embodiment of the invention is a preparation of antibodies which specifically binds to a polypeptide consisting essentially of the amino acid sequence shown in SEQ ID NO:4.

A further embodiment of the invention is a method of preparing a polypeptide consisting essentially of the amino acid sequence shown in SEQ ID NO:4. A host cell comprising an expression construct encoding the polypeptide is cultured under conditions whereby the polypeptide is expressed. The polypeptide is isolated.

The invention thus provides a human pyroglutamyl peptidase I which can be used to identify test compounds which may act, for example, as activators or inhibitors at the enzyme's active site. Human pyroglutamyl peptidase I and fragments thereof also are useful in raising specific antibodies which can block the enzyme and effectively reduce its activity.

BRIEF DESCRIPTION OF THE DRAWINGS

FIG. 1 shows the DNA-sequence of a mouse EST clone (SEQ ID NO. 1).

FIG. 2 shows the DNA-sequence of a mouse EST clone (SEQ ID NO. 2).

FIG. 3 shows the DNA-sequence encoding a pyroglutamyl peptidase-like enzyme polypeptide (SEQ ID NO. 3).

FIG. 4 shows the amino acid sequence deduced from the DNA-sequence of FIG. 3 (SEQ ID NO. 4).

FIG. 5 shows the amino acid sequence of the protein identified by the Accession NO. P42673 (SEQ ED NO. 5).

FIG. 6 shows the amino acid sequence of pfam/hmm/Peptidase_C15 (SEQ ID NO. 6).

FIG. 7 shows the DNA-sequence encoding a pyroglutamyl peptidase-like enzyme polypeptide (SEQ D NO. 7).

FIG. 8 shows the BLASTP alignment of human pyroglutamyl peptidase-like enzyme (SEQ ID NO. 4) with the protein identified from the Accession No. P42673 (SEQ ID NO. 5).

FIG. 9 shows the HMMPFAM alignment of human pyroglutamyl peptidase-like enzyme (SEQ ID NO. 4) against pfam|hmm|Peptidase_C15 (SEQ ID NO. 6).

DETAILED DESCRIPTION OF THE INVENTION

Figure 10:
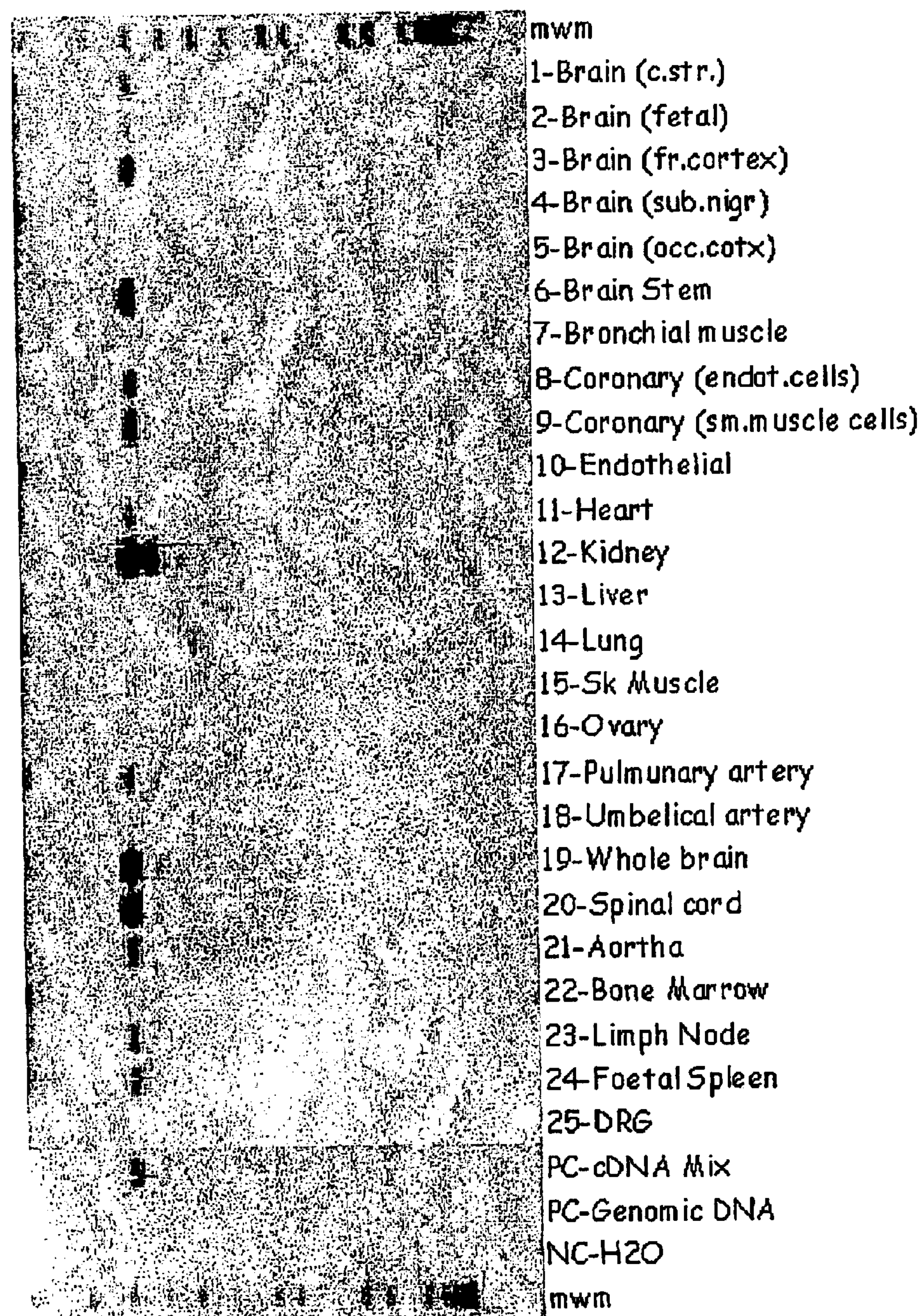
FIG. 10 shows the presence of PCR amplification products in human cDNA libraries.

The invention relates to an isolated polynucleotide encoding a pyroglutamyl peptidase-like enzyme polypeptide and being selected from the group consisting of:

a) a polynucleotide encoding a pyroglutamyl peptidase-like enzyme polypeptide comprising an amino acid sequence selected from the group consisting of:
   amino acid sequences which are at least about 50% identical to the amino acid sequence shown in SEQ ID NO. 4; and
   the amino acid sequence shown in SEQ ID NO. 4.

b) a polynucleotide comprising the sequence of SEQ ID NO. 3;

c) a polynucleotide which hybridizes under stringent conditions to a polynucleotide specified in (a) and (b);

d) a polynucleotide the sequence of which deviates from the polynucleotide sequences specified in (a) to (c) due to the degeneration of the genetic code; and e) a polynucleotide which represents a fragment, derivative or allelic variation of a polynucleotide sequence specified in (a) to (d).

Furthermore, it has been discovered by the present applicant that a novel pyroglutamyl peptidase-like enzyme, particularly a human pyroglutamyl peptidase-like enzyme, is a discovery of the present invention. Human pyroglutamyl peptidase-like enzyme comprises the amino acid sequence shown in SEQ ID NO. 4. Human pyroglutamyl peptidase-like enzyme is 28% identical over a 169 amino acid overlap to the pyrrolidoneoxylate peptidase identified by Accession No. P42673 (SEQ ID NO. 5) (FIG. 8). The identical amino acids of human pyroglutamyl peptidase-like enzyme include three residues that represent the active-site glu-cys-his catalytic triad found in pyroglutamyl peptidase (Odagaki et al., *Structure Fold Des*. 7, 399–411, 1999) (FIG. 8). Human pyroglutamyl peptidase-like enzyme also contains many identities to amino acids present in a hidden Markov model (hmm) of domains derived from pyroglutamyl peptidase-like sequences, as shown in FIG. 2. Mouse EST sequences (SEQ ID NOS:1 and 2), which are similar to the coding sequence shown in SEQ ID NO. 3, are expressed in brain, colon, kidney, and mammary gland.

The human pyroglutamyl peptidase-like enzyme of the invention is expected to be useful for the same purposes as previously identified pyroglutamyl peptidases. Thus, human pyroglutamyl peptidase-like enzyme can be used in therapeutic methods to treat disorders such as brain and spinal cord trauma, stroke, amyotropic lateral sclerosis, and spinocerebellar degeneration. Human pyroglutamyl peptidase-like enzyme also can be used to screen for human pyroglutamyl peptidase-like enzyme agonists and antagonists.

Polypeptides

Pyroglutamyl peptidase-like enzyme polypeptides according to the invention comprise at least 6, 10, 15, 25, 50, 75, 100, 125, 150, 175, 200 or 209 contiguous amino acids selected from the amino acid sequence shown in SEQ ID NO. 4 or a biologically active variant thereof as defined below. A pyroglutamyl peptidase-like enzyme polypeptide of the invention therefore can be a portion of a pyroglutamyl peptidase-like enzyme protein, a full-length pyroglutamyl peptidase-like enzyme protein, or a fusion protein comprising all or a portion of a pyroglutamyl peptidase-like enzyme protein.

Biologically Active Variants

Pyroglutamyl peptidase-like enzyme polypeptide variants which are biologically active, e.g., retain the ability to catalyze the removal of amino terminal pyroglutamate from a protein, also are pyroglutamyl peptidase-like enzyme polypeptides. Preferably, naturally or non-naturally occurring pyroglutamyl peptidase-like enzyme polypeptide variants have amino acid sequences which are at least about 30, 35, 40, 45, 50, 55, 60, 65, or 70, preferably about 75, 80, 85, 90, 96, 96, or 98% identical to the amino acid sequence shown in SEQ ID NO. 4 or a fragment thereof. Percent identity between a putative pyroglutamyl peptidase-like enzyme polypeptide variant and an amino acid sequence of SEQ ID NO. 4 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a pyroglutamyl peptidase-like enzyme polypeptide can be found using computer programs well known in the art, such as DNASTAR software. Whether an amino acid change results in a biologically active pyroglutamyl peptidase-like enzyme polypeptide can readily be determined by assaying for pyroglutamyl peptidase-like activity, as described for example, in de Gandarias et al., *Int. J. Dev. Biol*. 42, 10306, 1998, or Gallagher and O'Connor, *Int. J. Biochem. Cell Biol*. 30, 115, 1998.

Fusion Proteins

Fusion proteins are useful for generating antibodies against pyroglutamyl peptidase-like enzyme polypeptide amino acid sequences and for use in various assay systems. For example, fusion proteins can be used to identify proteins which interact with portions of a pyroglutamyl peptidase-like enzyme polypeptide. Protein affinity chromatography or library-based assays for protein-protein interactions, such as the yeast two-hybrid or phage display systems, can be used for this purpose. Such methods are well known in the art and also can be used as drug screens.

A pyroglutamyl peptidase-like enzyme polypeptide fusion protein comprises two polypeptide segments fused together by means of a peptide bond. The first polypeptide segment comprises at least 6, 10, 15, 25, 50, 75, 100, 125, 150, 175, or 200 contiguous amino acids of SEQ ID NO. 4 or of a biologically active variant, such as those described above. The first polypeptide segment also can comprise full-length pyroglutamyl peptidase-like enzyme protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the pyroglutamyl peptidase-like enzyme polypeptide-encoding sequence and the heterologous protein sequence, so that the pyroglutamyl peptidase-like enzyme polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO. 3 in proper reading fame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human pyroglutamyl peptidase-like enzyme polypeptide can be obtained using pyroglutamyl peptidase-like enzyme polypeptide polynucleotides (described below) to make suitable probes or primers for screening cDNA expression libraries from other species, such as mice, monkeys, or yeast, identifying cDNAs which encode homologs of pyroglutamyl peptidase-like enzyme polypeptide, and expressing the cDNAs as is known in the art.

Polynucleotides

A pyroglutamyl peptidase-like enzyme polynucleotide can be single- or double-stranded and comprises a coding sequence or the complement of a coding sequence for a pyroglutamyl peptidase-like enzyme polypeptide. A coding sequence for human pyroglutamyl peptidase-like enzyme is shown in SEQ ID NO. 3. This coding sequence is contained in the human genomic clone identified with Accession No. AK000215. Additional sequences 5' and 3' to the coding sequence are shown in SEQ ID NO. 7.

Degenerate nucleotide sequences encoding human pyroglutamyl peptidase-like enzyme polypeptides, as well as homologous nucleotide sequences which are at least about 50, 55, 60, 65, 70, preferably about 75, 90, 96, or 98% identical to the nucleotide sequence shown in SEQ ID NO. 3 also are pyroglutamyl peptidase-like enzyme polynucleotides. Percent sequence identity between the sequences of two polynucleotides is determined using computer programs such as ALIGN which employ the FAST algorithm, using an affine gap search with a gap open penalty of −12 and a gap extension penalty of −2. Complementary DNA (cDNA) molecules, species homologs, and variants of pyroglutamyl peptidase-like enzyme polynucleotides which encode biologically active pyroglutamyl peptidase-like enzyme polypeptides also are pyroglutamyl peptidase-like enzyme polynucleotides.

Identification of Polynuleotide Variants and Homologs

Variants and homologs of the pyroglutamyl peptidase-like enzyme polynucleotides described above also are pyroglutamyl peptidase-like enzyme polynucleotides. Typically, homologous pyroglutamyl peptidase-like enzyme polynucleotide sequences can be identified by hybridization of candidate polynucleotides to known pyroglutamyl peptidase-like enzyme polynucleotides under stringent conditions, as is known in the art. For example, using the following wash conditions -2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the pyroglutamyl peptidase-like enzyme polynucleotides disclosed herein also can be identified by making suitable probes or primers and screening cDNA expression libraries from other species, such as mice, monkeys, or yeast. Human variants of pyroglutamyl peptidase-like enzyme polynucleotides can be identified, for example, by screening human cDNA expression libraries. It is well known that the $T_m$ of a double-stranded DNA decreases by 1–1.5° C. with every 1% decrease in homology (Donner et al., *J. Mol. Biol.* 81, 123 (1973). Variants of human pyroglutamyl peptidase-like enzyme polynucleotides or pyroglutamyl peptidase-like enzyme polynucleotides of other species can therefore be identified by hybridizing a putative homologous pyroglutamyl peptidase-like enzyme polynucleotide with a polynucleotide having a nucleotide sequence of SEQ ID NO. 3 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to pyroglutamyl peptidase-like enzyme polynucleotides or their complements following stringent hybridization and/or wash conditions also are pyroglutamyl peptidase-like enzyme polynucleotides. Stringent wash conditions are well known and understood in the art and are disclosed, for example, in Sambrook et al., MOLECULAR CLONING: A LABORATORY MANUAL, 2d ed, 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a pyroglutamyl peptidase-like enzyme polynucleotide having a nucleotide sequence shown in SEQ ID NO. 3 or 7 or the complement thereof and a polynucleotide sequence which is at least about 50, 55, 60, 65, 70, 75, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m=81.5° C.-16.6(\log_{10}[Na^+])+0.41(\% G+C)-0.63(\% formamide)-600/l),$$ where l=the length of the hybrid in basepairs.

Stringent wash conditions include, for example, 4×S.C. at 65° C., or 50% formamide, 4×S.C. at 42° C, or 0.5×S.C., 0.1% SDS at 65° C. Highly stringent wash conditions include, for example, 0.2×S.C. at 65° C.

Preparation of Polynucleotides

A naturally occurring pyroglutamyl peptidase-like enzyme polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated pyroglutamyl peptidase-like enzyme polynucleotides. For example, restriction enzymes and probes can be used to isolate polynucleotide fragments which comprises pyroglutamyl peptidase-like enzyme nucleotide sequences. Isolated polynucleotides are in preparations which are free or at least 70, 80, or 90% free of other molecules. Pyroglutamyl peptidase-like enzyme cDNA molecules can be made with standard molecular biology techniques, using pyroglutamyl peptidase-like enzyme mRNA as a template. Pyroglutamyl peptidase-like enzyme cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesizes pyroglutamyl peptidase-like enzyme polynucleotides. The degeneracy of the genetic code allows alternate nucleotide sequences to be synthesized which will encode a pyroglutamyl peptidase-like enzyme polypeptide having, for example, an amino acid sequence shown in SEQ ID NO. 4 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic*. 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res*. 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic*. 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res*. 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions. When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Pyroglutamyl peptidase-like enzyme polypeptides can be obtained, for example, by purification from human cells, by expression of pyroglutamyl peptidase-like enzyme polynucleotides, or by direct chemical synthesis.

Protein Purification

Pyroglutamyl peptidase-like enzyme polypeptides can be purified from any cell which expresses the enzyme, including host cells which have been transfected with pyroglutamyl peptidase-like enzyme expression constructs. A purified pyroglutamyl peptidase-like enzyme polypeptide is separated from other compounds which normally associate with the pyroglutamyl peptidase-like enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified pyroglutamyl peptidase-like enzyme polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a pyroglutamyl peptidase-like enzyme polynucleotide, the polynucleotide can be inserted into an expression vector which contains the necessary elements for the transcription and translation of the inserted coding sequence. Methods which are well known to those skilled in the art can be used to construct expression vectors containing sequences encoding pyroglutamyl peptidase-like enzyme polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a pyroglutamyl peptidase-like enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a pyroglutamyl peptidase-like enzyme polypeptide, vectors based on SV40 or EBV can be used with an appropriate selectable marker.

Bacterial and Yeast Expression Systems

In bacterial systems, a number of expression vectors can be selected depending upon the use intended for the pyroglutamyl peptidase-like enzyme polypeptide. For example, when a large quantity of a pyroglutamyl peptidase-like enzyme polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the pyroglutamyl peptidase-like enzyme polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha actor, alcohol oxidase, and PGH can be used. For reviews, see Ausubel et al. (1989) and Grant et al., *Methods Enzymol.* 153, 516544, 1987.

Plant and Insect Expression Systems

If plant expression vectors are used, the expression of sequences encoding pyroglutamyl peptidase-like enzyme polypeptides can be driven by any of a number of promoters. For example, viral promoters such as the 35S and 19S promoters of CaMV can be used alone or in combination with the omega leader sequence from TMV (Takamatsu, *EMBO J.* 6,307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in McGRAW HILL YEARBOOK OF SCIENCE AND TECHNOLOGY, McGraw Hill, New York, N.Y., pp. 191–196,1992).

An insect system also can be used to express a pyroglutamyl peptidase-like enzyme polypeptide. For example, in one such system *Autographa californica* nuclear polyhedrosis virus (AcNPV) is used as a vector to express foreign genes in *Spodoptera frugiperda* cells or in *Trichoplusia larvae*. Sequences encoding pyroglutamyl peptidase-like enzyme polypeptides can be cloned into a non-essential region of the virus, such as the polyhedrin gene, and placed under control of the polyhedrin promoter. Successful insertion of pyroglutamyl peptidase-like enzyme polypeptides will render the polyhedrin gene inactive and produce recombinant virus lacking coat protein. The recombinant viruses can then be used to infect *S. frugiperda* cells or *Trichoplusia larvae* in which pyroglutamyl peptidase-like enzyme polypeptides can be expressed (Engelhard et al., *Proc. Nat. Acad. Sci.* 91, 3224–3227, 1994).

Mammalian Expression Systems

A number of viral-based expression systems can be used to express pyroglutamyl peptidase-like enzyme polypeptides in mammalian host cells. For example, if an adenovirus is used as an expression vector, sequences encoding pyroglutamyl peptidase-like enzyme polypeptides can be ligated into an adenovirus transcription/-translation complex comprising the late promoter and tripartite leader sequence. Insertion in a non-essential E1 or E3 region of the viral genome can be used to obtain a viable virus which is capable of expressing a pyroglutamyl peptidase-like enzyme polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g. liposomes, polycationic amino polymers, or vesicles).

Specific initiation signals also can be used to achieve more efficient translation of sequences encoding pyroglutamyl peptidase-like enzyme polypeptides. Such signals include the ATG initiation codon and adjacent sequences. In cases where sequences encoding a pyroglutamyl peptidase-like enzyme polypeptide, its initiation codon, and upstream sequences are inserted into the appropriate expression vector, no additional transcriptional or translational control signals may be needed. However, in cases where only coding sequence, or a figment thereo, is inserted, exogenous translational control signals (including the ATG initiation codon) should be provided The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ*. 20, 125–162, 1994).

Host Cells

A host cell strain can be chosen for its ability to modulate the expression of the inserted sequences or to process the expressed pyroglutamyl peptidase-like enzyme polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110–2209) and can be chosen to ensure the correct modification and processing of the foreign protein.

Stable expression is preferred for long-term, high-yield production of recombinant proteins. For example, cell lines which stably express pyroglutamyl peptidase-like enzyme polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced pyroglutamyl peptidase-like enzyme sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines.

These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in $tk^-$ or aprf cells, respectively. Also, antimetabolite, antibiotic, or herbicide resistance can be used as the basis for selection. For example, dhfr confers resistance to methotrexate (Wigler et al., *Proc. Natl. Acad Sci*. 77, 3567–70, 1980), npt confers resistance to the aminoglycosides, neomycin and G-418 (Colber arapin et al., *J. Mol. Biol*. 150, 1–14, 1981), and als and pat confer resistance to chlorsulfuron, and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad Sci*. 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol*. 55, 121–131, 1995).

Detecting Expression

Although the presence of marker gene expression suggests that the pyroglutamyl peptidase-like enzyme polynucleotide is also present, its presence and expression may need to be confirmed. For example, if a sequence encoding a pyroglutamyl peptidase-like enzyme polypeptide is inserted within a marker gene sequence, transformed cells containing sequences which encode a pyroglutamyl peptidase-like enzyme polypeptide can be identified by the absence of maker gene function. Alternatively, a marker gene can be placed in tandem with a sequence encoding a pyroglutamyl peptidase-like enzyme polypeptide under the control of a single promoter. Expression of the marker gene in response to induction or selection usually indicates expression of the pyroglutamyl peptidase-like enzyme polynucleotide.

Alternatively, host cells which contain a pyroglutamyl peptidase-like enzyme polynucleotide and which express a pyroglutamyl peptidase-like enzyme polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein For example, the presence of a polynucleotide sequence encoding a pyroglutamyl peptidase-like enzyme polypeptide can be detected by DNA-DNA or DNA-RNA hybridiztion or amplification using probes or fragments or fragments of polynucleotides encoding a pyroglutamyl peptidase-like enzyme polypeptide. Nucleic acid amplification-based assays involve the use of oligonucleotides selected from sequences encoding a pyroglutamyl peptidase-like enzyme polypeptide to detect transformants which contain a pyroglutamyl peptidase-like enzyme polynucleotide.

A variety of protocols for detecting and measuring the expression of a pyroglutamyl peptidase-like enzyme polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a pyroglutamyl peptidase-like enzyme polypeptide can be used, or a competitive binding assay can be employed. These and other assays are described in Hampton et at., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and ammo acid assays. Means for producing labeled hybridization or PCR probes for detecting sequences related to polynucleotides encoding pyroglutamyl peptidase-like enzyme polypeptides include oligolabeling, nick translation, end-labeling, or PCR amplification using a labeled nucleotide. Alternatively, sequences encoding a pyroglutamyl peptidase-like enzyme polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a pyroglutamyl peptidase-like enzyme polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art expression vectors containing polynucleotides which encode pyroglutamyl peptidase-like enzyme polypeptides can be designed to contain signal sequences which direct secretion of soluble pyroglutamyl peptidase-like enzyme polypeptides through a prokaryotic or eukauyotic cell membrane or which direct the membrane insertion of membrane-bound pyroglutamyl peptidase-like enzyme polypeptide.

As discussed above, other constructions can be used to join a sequence encoding a pyroglutamyl peptidase-like enzyme polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the pyroglutamyl peptidase-like enzyme polypeptide also can be used to facilitate purification. One such expression vector provides for expression of a fusion protein containing a pyroglutamyl peptidase-like enzyme polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying is the pyroglutamyl peptidase-like enzyme polypeptide from the fusion protein. Vectors which contain fusion proteins are disclosed in Kroll et al., *DNA Cell Biol.* 12, 441453, 1993.

Chemical Synthesis

Sequences encoding a pyroglutamyl peptidase-like enzyme polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a pyroglutamyl peptidase-like enzyme polypeptide itself can be produced using chemical methods to synthesize its amino acid sequence, such as by direct peptide synthesis using solid-phase techniques Merrifield, *J. Am. Chem. Soc.* 85, 2149–2154, 1963; Roberge et al., *Science* 269, 202–204, 1995). Protein synthesis can be performed using manual techniques or by automation Automated synthesis can be achieved, for example, using Applied Biosystems 431A Peptide Synthesizer (Perkin Elmer). Optionally, fragments of pyroglutamyl peptidase-like enzyme polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, W H Freeman and Co., New York, N.Y., 1983). The composition of a synthetic pyroglutamyl peptidase-like enzyme polypeptide can be confirmed by amino acid analysis or sequencing (e.g., the Edman degradation procedure; see Creighton, supra). Additionally, any portion of the amino acid sequence of the pyroglutamyl peptidase-like enzyme polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce pyroglutamyl peptidase-like enzyme polypeptide-encoding nucleotide sequences possessing non-naturally occurring codons. For example, codons preferred by a particular prokaryotic or erotic host can be selected to increase the rate of protein expression or to produce an RNA transcript having desirable properties such as a half-life which is longer than that of a transcript generated from the naturally occurring sequence.

The nucleotide sequences disclosed herein can be engineered using methods generally known in the art to alter pyroglutamyl peptidase-like enzyme polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth Antibodies Any type of antibody known in the art can be generated to bind specifically to an epitope of a pyroglutamyl peptidase-like enzyme polypeptide. "Antibody" as used herein includes intact immunoglobulin molecules, as well as fragments thereof such as Fab, $F(ab')_2$, and Fv, which are capable of binding an epitope of a pyroglutamyl peptidase-like enzyme polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a carnitine palmitoyltransferase I-like enzyme polypeptide can be used therapeutically, as well as in immunochemical assays, such as Western blots, ELISAs, radioimmunoassays, immunohistochemical assays, inmmunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a pyroglutamyl peptidase-like enzyme polypeptide provides a detection signal at least 5-, 10-, or 20-fold higher than a detection signal provided with other proteins when used in an immunochemical assay. Preferably, antibodies which specifically bind to pyroglutamyl peptidase-like enzyme polypeptides do not detect other proteins in immunochemical assays and can immunoprecipitate a pyroglutamyl peptidase-like enzyme polypeptide from solution.

Pyroglutamyl peptidase-like enzyme polypeptides can be used to immunize a mammal, such as a mouse, rat, rabbit, guinea pig, monkey, or human, to produce polygonal antibodies. If desired, a pyroglutamyl peptidase-like enzyme polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund=s adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a pyroglutamyl peptidase-like enzyme polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad Sci.* 80, 20262030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to a pyroglutamyl peptidase-like enzyme polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to pyroglutamyl peptidase-like enzyme polypeptides. Antibodies with related specificity, but of distinct idiotypic composition, can be generated by chain shuffling from random combinatorial immunoglobin libraries (Burton, *Proc. Natl. Acad Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81-91).

Antibodies which specifically bind to pyroglutamyl peptidase-like enzyme polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349,293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a pyroglutamyl peptidase-like enzyme polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of pyroglutamyl peptidase-like enzyme gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkyl-phosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, Meth. Mol. Biol. 26, 1–72, 1994; Uhlmann et al., *Chem. Rev.* 90, 543–583, 1990.

Modifications of pyroglutamyl peptidase-like enzyme gene expression can be obtained by designing antisense oligonucleotides which will form duplexes to the control, 5', or regulatory regions of the pyroglutamyl peptidase-like enzyme gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a pyroglutamyl peptidase-like enzyme polynucleotide. Antisense oligonucleotides which comprise, for example, 2, 3, 4, or 5 or more stretches of contiguous nucleotides which are precisely complementary to a pyroglutanyl peptidase-like enzyme polynucleotide, each separated by a stretch of contiguous nucleotides which are not complementary to adjacent pyroglutamnyl peptidase-like enzyme nucleotides, can provide sufficient targeting specificity for pyroglutamyl peptidase-like enzyme mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular pyroglutamyl peptidase-like enzyme polynucleotide sequence.

Antisense oligonucleotides can be modified without affecting their ability to hybridize to a pyroglutamyl peptidase-like enzyme polynucleotide. These modifications can be internal or at one or both ends of the antisense molecule. For example, intemucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., *Cech, Science* 236, 1532–1539; 1987; Coch, *Ann Rev. Biochem.* 59, 543–568; 1990, Cech, Curr. Opin. *Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a pyroglutamyl peptidase-like enzyme polynucleotide can be used to generate ribozymes which will specifically bind to mRNA transcribed from the pyroglutamyl peptidase-like enzyme polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a pyroglutamyl peptidase-like enzyme RNA target can be identified by scanning the target molecule for ribozyme cleavage sites which include the following sequences: GUA, GWU, and GUC. Once identified, short RNA sequences of between 15 and 20 ribonucleotides corresponding to the region of the target RNA containing the cleavage site can be evaluated for secondary structural features which may render the target inoperable. Suitability of candidate pyroglutamyl peptidase-like enzyme RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease pyroglutamyl peptidase-like enzyme expression. Alternatively, if it is desired that the cells stably retain the DNA construct, the construct can be supplied on a plasmid and maintained as a separate element or integrated into the genome of the cells, as is known in the art. A ribozyme-encoding DNA construct can include trascriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human pyroglutamyl peptidase-like enzyme. Such genes may represent genes which are differentially expressed in disorders including, but not limited to, brain and spinal cord trauma, stroke, neurodegenerative disorders, such as amyotropic lateral sclerosis or spinocerebellar degeneration, and coma or stupor due to anesthetics or an overdose of a drug. Further, such genes may represent genes which are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human pyroglutamyl peptidase-like enzyme gene or gene product may itself be tested for differential expression.

The degree to which expression differs in a normal versus a diseased state need only be large enough to be visualized via standard characterization techniques such as differential display techniques. Other such standard characterization techniques by which expression differences may be visaed include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique which does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomozynski, U.S. Pat. No. 4,843,155.

Transcripts within the collected RNA samples which represent RNA produced by differentially expressed genes are identified by methods well known to those of skill in the art. They include, for example, differential screcung (edder et al., *Proc. Natl. Acad Sci. U.S.A.* 85, 208–12, 1988), subtractive hybridization (Hedrick et al., *Nature* 308, 149–53; Lee et al., *Proc. Natl. Acad Sci. U.S.A.* 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human pyroglutamyl peptidase-like enzyme. For example, treatment may include a modulation of expression of the differentially expressed genes and/or the gene encoding the human pyroglutamyl peptidase-like enzyme. The differential expression information may indicate whether the expression or activity of the differentially expressed gene or gene product or the human pyroglutamyl peptidase-like enzyme gene or gene product are up-regulated or down-regulated.

Screening Methods

The invention provides assays for screening test compounds which bind to or modulate the activity of a pyroglutamyl peptidase-like enzyme polypeptide or a pyroglutamyl peptidase-like enzyme polynucleotide. A test compound preferably binds to a pyroglutamyl peptidase-like enzyme polypeptide or polynucleotide. More preferably, a test compound decreases or increases pyroglutamyl peptidase-like activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad Sci.* 97, 6378–6382, 1990; Felici, *J. Mol. Biol.* 222,301–310, 1991; and Ladner, U.S. Pat. 5,223,409).

High Throuhput Screening

Test compounds can be screened for the ability to bind to pyroglutamyl peptidase-like enzyme polypeptides or polynucleotides or to affect pyroglutamyl peptidase-like enzyme activity or pyroglutamyl peptidase-like enzyme gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 1. In addition to the plates, many instruments, materials, puppeteers, robotics, plate washers, and plate readers are commercially available to fit the 96-well format Alternately, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support When samples are introduced to the porous matrix they diffuse sufficiently slowly, such that the assays can be performed without the test samples running together.

Binding Assays

For binding assays, the test compound is preferably a small molecule which binds to and occupies, for example, the active site of the pyroglutamyl peptidase-like enzyme polypeptide, such that normal biological activity is prevented. Examples of such small molecules include, but are not limited to, small peptides or peptide-like molecules.

In binding assays, either the test compound or the pyroglutamyl peptidase-like enzyme polypeptide can comprise a detectable label, such as a fluorescent, radioisotopic, chemiluminescent, or enzymatic label, such as horseradish peroxidase, alkaline phosphatase, or luciferase. Detection of a test compound which is bound to the pyroglutamyl peptidase-like enzyme polypeptide can then be accomplished, for example, by direct counting of radioemmission, by scintillation counting, or by determining conversion of an appropriate substrate to a detectable product.

Alternatively, binding of a test compound to a pyroglutamyl peptidase-like enzyme polypeptide can be determined without labeling either of the interactants. For example, a microphysiometer can be used to detect binding of a test compound with a pyroglutamyl peptidase-like enzyme polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a pyroglutamyl peptidase-like enzyme polypeptide (McConnell et al., *Science* 257, 1906–1912, 1992).

Determining the ability of a test compound to bind to a pyroglutamyl peptidase-like enzyme polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (eg., BIAcore™). Changes in the optical phenomenon surface plasmon resonance (SPR) can be used as an indication of real-time reactions between biological molecules.

In yet another aspect of the invention, a pyroglutamyl peptidase-like enzyme polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO 941/0300), to identify other proteins which bind to or interact with the pyroglutamyl peptidase-like enzyme polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a pyroglutamyl peptidase-like enzyme polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the pyroglutamyl peptidase-like enzyme polypeptide.

It may be desirable to immobilize either the pyroglutamyl peptidase-like enzyme polypeptide (or polynucleotide) or the test compound to facilitate separation of bound from unbound forms of one or both of the interactants, as well as to accommodate automation of the assay. Thus, either the pyroglutamyl peptidase-like enzyme polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the pyroglutamyl peptidase-like enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a pyroglutamyl peptidase-like enzyme polypeptide (or polynucleotide) can be accomplished in any vessel suitable for containing the reactants. Examples of such vessels include microtiter plates, test tubes, and microcentrifuge tubes.

In one embodiment, the pyroglutamyl peptidase-like enzyme polypeptide is a fusion protein comprising a domain that allows the pyroglutamyl peptidase-like enzyme polypeptide to be bound to a solid support For example, glutathione-S-transferase fusion proteins can be adsorbed onto glutathione sepharose beads (Sigma Chemical St. Louis, Mo.) or glutathione derivatized microtiter plates, which are then combined with the test compound or the test compound and the non-adsorbed pyroglutamyl peptidase-like enzyme polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a pyroglutamyl peptidase-like enzyme polypeptide (or polynucleotide) or a test compound can be immobilized utilizing conjugation of biotin and streptavidin. Biotinylated pyroglutamyl peptidase-like enzyme polypeptides (or polynucleotides) or test compounds can be prepared from biotin-NHS (N-hydroxysuccimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a pyroglutamyl peptidase like enzyme polypeptide, polynucleotide, or a test compound, but which do not interfere with a desired binding site, such as the active site of the pyroglutamyl peptidase-like enzyme polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the pyroglutamyl peptidase-like enzyme polypeptide or test compound, enzyme-linked assays which rely on detecting an activity of the pyroglutamyl peptidase-like enzyme polypeptide, and SDS gel electrophoresis under non-reducing conditions.

Screening for test compounds which bind to a pyroglutamyl peptidase-like enzyme polypeptide or polynucleotide also can be carried out in an intact cell. Any cell which comprises a pyroglutamyl peptidase-like enzyme polypeptide or polynucleotide can be used in a cell-based assay system. A pyroglutamyl peptidase-like enzyme polynucleotide can be naturally occurring in the cell or can be introduced using techniques such as those described above. Binding of the test compound to a pyroglutamyl peptidase-like enzyme polypeptide or polynucleotide is determined as described above.

Enzyme Assays

Test compounds can be tested for the ability to increase or decrease the pyroglutamyl peptidase activity of a human pyroglutamyl peptidase-like enzyme polypeptide. For example, pyroglutamyl peptidase I activity can be measured as described in de Gandarias et al., *Int. J. Dev. Biol.* 42, 10306, 1998; and pyroglutamyl peptidase II activity can be measured as described in Gallagher and O'Connor. *Int. J. Biochem. Cell. Biol.* 30, 115,1998.

Enzyme assays can be carried out after contacting either a purified pyroglutamyl peptidase-like enzyme polypeptide, a cell membrane preparation, or an intact cell with a test compound. A test compound which decreases a pyroglutamyl peptidase activity of a pyroglutamyl peptidase-like enzyme polypeptide by at least about 10, preferably about 50, more preferably about 75, 90, or 100% is identified as a potential therapeutic agent for decreasing pyroglutamyl peptidase-like enzyme activity. A test compound which increases a pyroglutamyl peptidase activity of a human pyroglutamyl peptidase-like enzyme polypeptide by at least about 10, preferably about 50, more preferably about 75, 90, or 100% is identified as a potential therapeutic agent for increasing human pyroglutamyl peptidase-like enzyme activity.

Gene Expression

In another embodiment, test compounds which increase or decrease pyroglutamyl peptidase-like enzyme gene expression are identified. A pyroglutamyl peptidase-like enzyme polynucleotide is contacted with a test compound, and the expression of an RNA or polypeptide product of the pyroglutamyl peptidase-like enzyme polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of pyroglutamyl peptidase-like enzyme mRNA or polypeptide expression in the cells can be determined by methods well known in the art for detecting mRNA or polypeptide. Either qualitative or quantitative methods can be used. The presence of polypeptide products of a pyroglutamyl peptidase-like enzyme polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a pyroglutamyl peptidase-like enzyme polypeptide.

Such screening can be carried out either in a cell-free assay system or in an intact cell. Any cell which expresses a pyroglutamyl peptidase-like enzyme polynucleotide can be used in a cell-based assay system. The pyroglutamyl peptidase-like enzyme polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions which can be administered to a patient to achieve a therapeutic effect. Pharmaceutical compositions of the invention can comprise, for example, a pyroglutamyl peptidase-lice enzyme polypeptide, pyroglutamyl peptidase-like enzyme polynucleotide, ribozymes or antisense oligonucleotides, antibodies which specifically bind to a pyroglutamyl peptidase-like enzyme polypeptide, or mimetics, agonists, antagonists, or inhibitors of a pyroglutamyl peptidase-like enzyme polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the prepatation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Pyroglutamyl peptidases are found in a number of tissues, including brain, colon, kidney and pancreas where they function to cleave pyroglutamyl from peptide substrates (Fuse et al., *Am. J. Physiol.* 259, E787, 1990; Heuer et al. *Eur. J. Neurosci.* 10, 1465, 1998). Many of the pyroglutamyl peptidase substrates are peptide hormones, such as thyrotropin releasing hormone (TRH), which functions as a neurotransmitter and/or a neuromodulator (Faden, U.S. Pat. No. 5,686,420). TRH has been implicated in a number of neurological disorders, including brain and spinal cord trauma; stroke; neurodegenerative disorders, such as amyotropic lateral sclerosis or spinocerebellar degeneration; and coma or stupor due to anesthetics or an overdose of a drug (Faden, U.S. Pat. No. 5,686,420). The regulation of TRH levels occurs, in part, through pyroglutamate peptidase cleavage of its amino terminal pyroglutamate. The distribution of pyroglutamate peptidases, coupled with their cleavage of peptide hormones, suggests that these enzymes contribute to neurological and neurodegenerative diseases. Compounds directed to the regulation of human pyroglutamate peptidase-like enzyme may therefore prove useful as therapeutic agents for diseases such as brain and spinal cord trauma, amyotropic lateral sclerosis or spinocerebellar degeneration, and coma due to anesthetics.

The peptide hormone TRH appears to antagonize the actions of autodestructive biochemical substances, such as endogenous opioids, that accompany brain and spinal cord trauma (Faden, U.S. Pat. No. 5,686,420). In addition to these traumas, such autodestructive biochemicals are associated with neurologic disorders such as stroke; systic, hypovolemic or anaphylactic shock; neurodegenerative disorders such as amyotropic lateral sclerosis or spinocerebellar degeneration; and unconsciousness or subconsciousness due to anesthetics or overdoses These beneficial antagonistic effects of TRH are limited by the rapid metabolism of TRH that occurs to either endogenous TRH or exogenously administered TRH. Compounds that inhibit pyroglutamyl peptidase cleavage of TRH are likely to reduce the rapid metabolism of TRH. Inhibitors of human pyroglutamyl peptidase-like enzyme may therefore prove useful in the treatment of brain and spinal cord trauma, stroke, shock, and neurodegenerative disorders.

Disorders of the nervous system which may be treated include brain injuries, cerebrovascular diseases and their consequences, Parkinson's disease, corticobasal degeneration, rotor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis also can be treated. Similarly, it is possible to treat cognitive-related disorders, such as mild cognitive impairment, age-associated memory impairment, age-related cognitive decline, vascular cognitive impairment, attention deficit disorders, attention deficit hyperactivity disorders, and memory distances in children with learning disabilities, by regulating the activity of human pyroglutamate peptidase like protein.

A deficiency of TRH has been observed to occur in cases of hypothyroidism (Nimi et al., *Arch. Dis. Child.* 57, 877, 1982; Katakami et al., *J. Endocr. Invest.* 7, 231, 1984). While the mechanism of the TRH deficiency observed in these instances is not known, inhibition of pyroglutamyl peptidase activity that cleaves pyroglutamyl from TRH may assist in alleviating the TRH deficiency. Compounds that inhibit human pyroglutamyl peptidase-like enzyme are therefore potential therapeutics against TRH deficiency.

Deficiency of thyrotropin releasing hormone is associated with hypothyroidism and may be detrimental in disorders of the central nervous system, such as brain and spinal cord trauma and neurodegenerative diseases (Niimi et al., *Arch. Dis. Child.* 57, 877, 1982; Katkami et al., *J. Endocr. Invest.* 7, 231, 1984; Faden, U.S. Pat. 5,686,420). Inhibition of pyroglutamyl peptidase cleavage of TRH may prove useful in the treatment of TRH deficiency.

The ability of inhibition of pyroglutamyl peptidase to raise TRH levels has been observed in vitro with rat brain tissue. Isolated pyroglutamyl peptidase II is inhibited in vitro by the compound N-1-carboxy-2-phenylethyl (Nimbenzyl)-histidyl-beta-naphthylamide (CPHNA) (Charli et al., *Neuropeptides*, 14, 191, 1989). Administration of CPHNA to rat brain hypothalamic tissue in vitro stimulated the recovery of TRH from the brain tissue (Charli et al., *Neuropeptides*, 14, 191, 1989). Moreover, brain tissue that had relatively higher levels of pyroglutamyl peptidase II activity commensurately gave a higher recovery of TRH when treated with the pyroglutanyl peptidase II inhibitor. The ability of a pyroglutamyl peptidase inhibitor to increase peptide hormone levels from brain tissue in vitro suggests that such an inhibitor may be effective at doing so in vivo as well Compounds that inhibit human pyroglutamyl peptidase-like enzyme may therefore prove useful in raising peptide hormone levels in vivo for the treatment of conditions where an increase in peptide hormone levels would be beneficial.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a pyroglutamyl peptidase-like enzyme polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects pyroglutamyl peptidase-like enzyme activity can be administered to a human cell, either in vitro or in vivo, to reduce pyroglutamyl peptidase-like enzyme activity. The reagent preferably binds to an expression product of a human pyroglutamyl peptidase-like enzyme gene. If the expression product is a protein, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 $\mu$g of DNA per 16 nmole of liposome delivered to about $10^6$ cells, more preferably about 1.0 $\mu$g of DNA per 16 nmole of liposome delivered to about $10^6$ cells, and even more preferably about 2.0 $\mu$g of DNA per 16 nmol of liposome delivered to about $10^6$ cells. Preferably, a liposome is between about 100 and 500 nm, more preferably between about 150 and 450 mm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 $\mu$g to about 10 $\mu$g of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases pyroglutamyl peptidase-like enzyme activity relative to the pyroglutamyl peptidase-like enzyme activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of poly-nucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAF or calcium phosphate-mediated transfection.

Effective in vivo dosages of an antibody are in the range of about 5 μg to about 50 μg/kg, about 50 μg to about 5 mg/kg, about 100 μg to about 500 μg/kg of patient body weight, and about 200 to about 250 μg/kg of patient body weight. For administration of polynucleotides encoding single-chain antibodies, effective in vivo dosages are in the range of about 100 ng to about 200 ng, 500 ng to about 50 mg, about 1 μg to about 2 mg, about 5 μg to about 500 μg, and about 20 μg to about 100 μg of DNA.

If the expression product is mRNA, the reagent is preferably an antisense oligonucleotide or a ribozyme. Polynucleotides which express antisense oligo-nucleotides or ribozymes can be introduced into cells by a variety of methods, as described above.

Preferably, a reagent reduces expression of a pyroglutamyl peptidase-like enzyme gene or the activity of a pyroglutamyl peptidase-like enzyme polypeptide by at least about 10, preferably about 50, more preferably about 75, 90, or 100% relative to the absence of the reagent. The effectiveness of the mechanism chosen to decrease the level of expression of a pyroglutamyl peptidase-like enzyme gene or the activity of a pyroglutamyl peptidase-like enzyme polypeptide can be assessed using methods well known in the art, such as hybridization of nucleotide probes to pyroglutamyl peptidase-like enzyme-specific mRNA, quantitative RT-PCR, immunologic detection of a pyroglutamyl peptidase-like enzyme polypeptide, or measurement of pyroglutamyl peptidase-like enzyme activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human pyroglutamyl peptidase-like enzyme also can be used in diagnostic assays for detecting diseases and abnormalities or susceptibility to diseases and abnormalities related to the presence of mutations in the nucleic acid sequences which encode the enzyme. For example, differences can be determined between the cDNA or genoric sequence encoding pyroglutamyl peptidase-like enzyme in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad Sci. U.S.A.* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a pyroglutamyl peptidase-like enzyme also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Pyroglutamyl Peptidase-like Enzyme Activity

The polynucleotide of SEQ ID NO. 3 is inserted into the expression vector pCEV4 and the expression vector pCEV4-pyroglutamyl peptidase-like enzyme polypeptide obtained is transfected into human embryonic kidney 293 cells. From these cells extracts are obtained and the pyroglutamyl peptidase-like enzyme activity is determined with the chromogenic compound Pyr-MCA (L-Pyroglutamic Acid 4-Methyl-Coumaryl-7-Amide) as substrate. Enzyme specific activities are expressed in released coumaryl compound from the substrate. The optimal conditions for the pyroglutamyl peptidase assay are 37° C. and pH 6,6. The concentration of the final reaction product, released coumaryl compound, is determined at 355 nm with a fluorimeter (PerSeptive Biosystems, Inc.) using the 395 nm exitation/530 nm emission filter set. It is shown that the polypeptide of SEQ ID NO. 4 has a pyroglutamyl peptidase-like enzyme activity.

EXAMPLE 2

Expression of Recombinant Human Pyroglutamyl Peptidase-like Enzyme

The Pichia pastoris expression vector pPICZB (Invitrogen, San Diego, Calif.) is used to produce large quantities of recombinant human pyroglutamyl peptidase polypeptides in yeast. The pyroglutamyl peptidase-like enzyme-encoding DNA sequence is derived from SEQ ID NO. 3. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human pyroglutamyl peptidase-like enzyme polypeptide is obtained.

EXAMPLE 3

Identification of Test Compounds That Bind to Pyroglutamyl Peptidase-like Enzyme Polypeptides Purified pyroglutamyl peptidase-like enzyme polypeptides comprising a glutathione-S-transferase protein and absorbed onto glutathione-derivatized wells of 96-well microtiter plates are contacted with test compounds from a small molecule library at pH 7.0 in a physiological buffer solution. pyroglutamyl peptidase-like enzyme polypeptides comprise the amino acid sequence shown in SEQ ID NO. 4. The test compounds comprise a fluorescent tag. The samples are incubated for 5 minutes to one hour. Control samples are incubated in the absence of a test compound.

The buffer solution containing the test compounds is washed from the wells. Binding of a test compound to a pyroglutamyl peptidase-like enzyme polypeptide is detected by fluorescence measurements of the contents of the wells. A test compound which increases the fluorescence in a well by at least 15% relative to fluorescence of a well in which a test compound is not incubated is identified as a compound which binds to a pyroglutamyl peptidase-like enzyme polypeptide.

EXAMPLE 4

Identification of a Test Compound which Decreases Pyroglutamyl Peptidase-like Enzyme Gene Expression A test compound is administered to a culture of human cells transfected with a pyroglutamyl peptidase-like enzyme expression construct and incubated at 37° C. for 10 to 45 minutes. A culture of the same type of cells which have not been transfected is incubated for the same time without the test compound to provide a negative control. RNA is isolated from the two cultures as described in Chirgwin et al., *Biochem.* 18, 5294–99, 1979). Northern blots are prepared using 20 to 30 $\mu$g total RNA and hybridized with a $^{32}$P-labeled pyroglutamyl peptidase-like enzyme-specific probe at 6° C. in Express-hyb (CLONTECH). The probe comprises at least 11 contiguous nucleotides selected from the complement of SEQ D NO. 3. A test compound which decreases the pyroglutamyl peptidase-like enzyme-specific signal relative to the signal obtained in the absence of the test compound is identified as an inhibitor of pyroglutamyl peptidase-like enzyme gene expression.

EXAMPLE 5

Expression of Pyroglutamyl Peptidase-like Enzyme in Various Human Tissues

Human cDNA phage libraries (Stratagene) were ordered in a "human tissue panel LA" (unless differently specified) as described in Tab.1.

0.5 $\mu$l of each library purchased sample were used as template in PCR analysis regardless the title (phage/ml) for non quantitative expression analysis. In addition a positive control PCR reaction was performed with about 20 ng of human genomic DNA as template and a negative control was performed with no template.

Standard PCR procedure were as indicated by Perkin Elmer. PCR protocol was as follows:

PCR reaction mix:

0.5 $\mu$l template

1× Gold PCR Buffer (Perkin Elmer)

0.2 mM dNTPs (Pharmacia)

1.5 mMMgC12 (Perkin Elmer)

0.5 $\mu$M forward primer 0.5 $\mu$M backward primer 2.5 $\mu$M AmpliTaq Gold DNA Polymerase (Perkin Elmer)

to 25 $\mu$l final reaction volume with sterile $H_2O$.

Amplification protocol performed in Perlin Elmer 9700 thermocycler.

1 time the following step:

pre PCR 9' at 94° C.

40 times the following steps:

denaturation 30" at 94° C.

annealing 1' at 65° C.

elongation 30" at 72° C.

Expected length of specific PCR product: 300 bp

Amplification products were analysed by electrophoresis on 2% agarose (SeaKem LE agarose, FMC bioproducts) gel in 1×TAE running buffer following standard procedure, as described by Maniatis et al.

PCR amplification products of the expected size were detectable in the lanes corresponding to brain, coronary artery, heart, kidney, pulmonary artery, spinal cord, aortha aorta, lymph node, and fetal spleen phage libraries. The results are shown in FIG. 10.

In order to check PCR product identity a mixture of the amplification products obtained was used for restriction analysis with the enzyme PvuII (BioLabs) following purchasers indications. Restriction fragments were analysed by electrophoresis on 2% agarose (SeaKem LE agarose, FMC bioproducts) gel in 1×TAE running buffer following standard procedure, as described by Maniatis et al.

TABLE 1

| Library | Description | Catalogue No. |
|---|---|---|
| Brain (corpus striatum) | Caudate and putamen, males, 57 & 63 years old | 936213 |
| Brain (foetal) | Male and female, Caucasian | 937227 |
| Brain (frontal cortex) | Female, 85 years old | 936212 |
| Brain (substantia nigra) | Male and female, 60 years old | 936210 |
| Brain (occipital cortex) | Female, 85 years old | 936211 |
| Brain stem | Female, 2 years old | 935206 |
| Bronchial muscle | Human bronchial/tracheal smooth muscle primary cells | 780032 |
| Coronary | Coronary artery endothelial primary cells | 780025 |
| Coronary | Coronary artery smooth muscle primary cells | 780029 |
| Endothelial | Microvascular endothelial primary cells | 780028 |
| Heart | 12 pooled, 19–50 years old, male/female Caucasian | 937257 |
| Kidney | 8 pooled, whole kidney from 24–55 years old, male/female, Caucasian | 937250 |
| Liver | Normal, 38 years old, Caucasian | 937241 |
| Lung | Male, 72 years old, normal | 937210 |
| Muscle (skeletal) | Female, 19 years old | 936215 |
| Ovary | Normal, 49 years old, Caucasian | 937217 |
| Pulmonary artery endothelial | Pulmonary artery endothelial primary cells | 780027 |
| Umbilical artery endothelial cells | Umbilical artery endothelial cells | 780023 |
| Whole Brain | Whole brain 60 year | HL5018t Clontech |
| Spinal chord | Whole, pooled from 26 male/female, 16–75 years | HL5001b Clontech |
| Aorta | Whole thoracic (intima & media) pooled from 1 female/3 male | HL1136a Clontech |

TABLE 1-continued

| Library | Description | Catalogue No. |
|---|---|---|
| Bone Marrow | Pooled from 51 male/female | HL5034t Clontech |
| Lymph Node | Whole lymph nodes pooled 34 male/female | HL5036t Clontech |
| Foetal spleen | Pooled from 6 spleens (13–22 weeks gestation) | 937262 |
| DRG | | 11137-015 Life Technologies |

What is claimed is:

1. A method of screening for candidate therapeutic agents, comprising the steps of:

contacting a protein comprising the amino acid sequence shown in SEQ ID NO:4 with a test compound;

assaying for binding between the protein and the test compound; and identifying a test compound that binds to the protein as a candidate therapeutic agent that may be useful for treating a disorder selected from the group consisting of a nervous system disorder and hypothyroidism.

2. The method of claim 1 wherein either the test compound or the protein comprises a detectable label.

3. The method of claim 1 wherein either the test compound or the protein is bound to a solid support.

* * * * *

UNITED STATES PATENT AND TRADEMARK OFFICE

CERTIFICATE OF CORRECTION

PATENT NO. : 6,821,745 B2
APPLICATION NO. : 10/380105
DATED : November 23, 2004
INVENTOR(S) : Timothy J. Smith It is certified that error appears in the above-identified patent and that said Letters Patent is hereby corrected as shown below:

On the Title Page, References Cited section (56), Other Publications:
In the first column, third reference:
Please replace "(PGPEPI gene)" with --(PGPEP1 gene)--

On the Title Page, References Cited section (56), Other Publications:
In the second column, first reference:
Please replace the printed reference with --Database EMBL "Online" Feb. 22, 2000. Sugano S. et al "Homo sapiens cDNA FLJ20208 fis, clone CoLF1623" Database accession no. AK000215 (XP002199513)--

On the Title Page, References Cited section (56), Other Publications:
In the second column, third reference:
Please replace "Schomberg" with --Schomburg--

On the Title Page, References Cited section (56), Other Publications:
In the second column, fourth reference:
Please replace "aminopeptidase:" with --aminopeptidases:--

Signed and Sealed this

Thirteenth Day of November, 2007

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 540
<212> TYPE: DNA
<213> ORGANISM: Homo sapiens

<400> SEQUENCE: 1

ttccaccatg gagcagccgc ggaaggcggt agtggtaacc ggattcggcc cttttgggga     60

gcatactgtg aatgccagct ggatcgctgt ccaggagctg gagaagctgg gcctcgggga    120

cagcgtggac ctgcatgtgt acgagatccc cgtggaatac cagacggtgc agaggctcat    180

cccagcactg tgggagaagc acagccccca gctcgtagtg catgttgggg tgtcgggcat    240

ggccaccaca gtgacgctgg aaaaatgtgg gcacaacaag ggttacaaag gactggataa    300

ttgccggttc tgccccggct ctcagtgctg cgtggaggat ggtcccgaga gcatcgactc    360

catcatcgac atggacgccg tgtgcaaaag ggtgaccaca ctgggactgg acgtgtctgt    420

taccatctcc caggatgctg gcaggtatct gtgtgacttc acgtattata catcgctcta    480

ccagggccgc ggccgctccg cttttgtcca cgtgccccca ctggtaagcc ctacaacgcc    540


<210> SEQ ID NO 2
<211> LENGTH: 540
<212> TYPE: DNA
<213> ORGANISM: Homo sapiens

<400> SEQUENCE: 2

ttccaccatg gagcagccgc ggaaggcggt agtggtaacc ggattcggcc cttttgggga     60

gcatactgtg aatgccagct ggatcgctgt ccaggagctg gagaagctgg gcctcgggga    120

cagcgtggac ctgcatgtgt acgagatccc cgtggaatac cagacggtgc agaggctcat    180

cccagcactg tgggagaagc acagccccca gctcgtagtg catgttgggg tgtcgggcat    240

ggccaccaca gtgacgctgg aaaaatgtgg gcacaacaag ggttacaaag gactggataa    300

ttgccggttc tgccccggct ctcagtgctg cgtggaggat ggtcccgaga gcatcgactc    360

catcatcgac atggacgccg tgtgcaaaag ggtgaccaca ctgggactgg acgtgtctgt    420

taccatctcc caggatgctg gcaggtatct gtgtgacttc acgtattata catcgctcta    480

ccagggccgc ggccgctccg cttttgtcca cgtgccccca ctggtaagcc ctacaacgcc    540


<210> SEQ ID NO 3
<211> LENGTH: 630
<212> TYPE: DNA
<213> ORGANISM: Homo sapiens
```

-continued

<400> SEQUENCE: 3

```
atggagcagc cgaggaaggc ggtggtagtg acgggatttg gcccttttgg ggaacacacc     60
gtgaacgcca gttggattgc agttcaggag ctagaaaagc taggccttgg cgacagcgtg    120
gacctgcatg tgtacgagat tccggttgag taccaaacag tccagagact catccccgcc    180
ctgtgggaga agcacagtcc acagctggtg gtgcatgtgg gggtgtcagg catggcgacc    240
acagtcacac tggagaaatg tggacacaac aagggctaca aggggctgga caactgccgc    300
ttttgccccg gctcccagtg ctgcgtggag gacgggcctg aaagcattga ctccatcatc    360
gacatggatg ctgtgtgcaa gcgagtcacc acgttgggcc tggatgtgtc ggtgaccatc    420
tcgcaggatg ccggcagata tctctgcgac tttacctact acacctcttt gtaccagagt    480
cacggtcgat cagccttcgt ccacgtgccc ccactgggga agccgtacaa cgcggaccag    540
ctgggcaggg cactgagagc catcattgag gagatgttgg acctcctgga gcagtcagag    600
ggcaaaatca actattgcca caaacactga                                     630
```

<210> SEQ ID NO 4
<211> LENGTH: 209
<212> TYPE: PRT
<213> ORGANISM: Homo sapiens

<400> SEQUENCE: 4

```
Met Glu Gln Pro Arg Lys Ala Val Val Val Thr Gly Phe Gly Pro Phe
1               5                   10                  15

Gly Glu His Thr Val Asn Ala Ser Trp Ile Ala Val Gln Glu Leu Glu
            20                  25                  30

Lys Leu Gly Leu Gly Asp Ser Val Asp Leu His Val Tyr Glu Ile Pro
        35                  40                  45

Val Glu Tyr Gln Thr Val Gln Arg Leu Ile Pro Ala Leu Trp Glu Lys
    50                  55                  60

His Ser Pro Gln Leu Val Val His Val Gly Val Ser Gly Met Ala Thr
65                  70                  75                  80

Thr Val Thr Leu Glu Lys Cys Gly His Asn Lys Gly Tyr Lys Gly Leu
                85                  90                  95

Asp Asn Cys Arg Phe Cys Pro Gly Ser Gln Cys Cys Val Glu Asp Gly
            100                 105                 110

Pro Glu Ser Ile Asp Ser Ile Ile Asp Met Asp Ala Val Cys Lys Arg
        115                 120                 125

Val Thr Thr Leu Gly Leu Asp Val Ser Val Thr Ile Ser Gln Asp Ala
    130                 135                 140

Gly Arg Tyr Leu Cys Asp Phe Thr Tyr Tyr Thr Ser Leu Tyr Gln Ser
145                 150                 155                 160

His Gly Arg Ser Ala Phe Val His Val Pro Pro Leu Gly Lys Pro Tyr
                165                 170                 175

Asn Ala Asp Gln Leu Gly Arg Ala Leu Arg Ala Ile Ile Glu Glu Met
            180                 185                 190

Leu Asp Leu Leu Glu Gln Ser Glu Gly Lys Ile Asn Tyr Cys His Lys
        195                 200                 205

His
```

<210> SEQ ID NO 5
<211> LENGTH: 213
<212> TYPE: PRT
<213> ORGANISM: Homo sapiens

<400> SEQUENCE: 5

```
Met Arg Ile Val Leu Leu Thr Gly Phe Glu Pro Phe Asp Gln Asp Pro
1               5                   10                  15

Val Asn Pro Ser Trp Glu Ala Val Arg Gln Leu Asp Gly Val Gln Leu
            20                  25                  30

Gly Ser Asp Val Lys Ile Val Ala Arg Arg Leu Pro Cys Ala Phe Ala
        35                  40                  45

Thr Ala Gly Glu Cys Leu Thr Arg Leu Ile Asp Glu Leu His Pro Ala
    50                  55                  60

Met Val Ile Ala Thr Gly Leu Gly Pro Gly Arg Ser Asp Ile Ser Val
65                  70                  75                  80

Glu Arg Val Ala Ile Asn Ile Asn Asp Ala Arg Ile Pro Asp Asn Leu
                85                  90                  95

Gly Glu Gln Pro Ile Asp Thr Ala Val Val Ala Asp Gly Pro Ala Ala
            100                 105                 110

Phe Phe Thr Thr Leu Pro Ile Lys Ala Met Val Lys Ala Val Arg Glu
        115                 120                 125

Ala Gly Ile Ala Ala Ser Val Ser Gln Thr Ala Gly Thr Phe Val Cys
    130                 135                 140

Asn Gln Val Phe Tyr Leu Leu Gln His Ala Leu Ala Gly Ser Gly Val
145                 150                 155                 160

Arg Ser Gly Phe Ile His Val Pro Phe Leu Pro Glu Gln Val Ala Gly
                165                 170                 175

Ser Gln Arg Pro Ser Met Ala Leu Asp Ala Met Val Ala Gly Leu Gln
            180                 185                 190

Ala Ala Val Leu Thr Ala Trp His Thr Pro Val Asp Val Lys Glu Ala
        195                 200                 205

Gly Gly Gln Val Ser
    210
```

<210> SEQ ID NO 6
<211> LENGTH: 212
<212> TYPE: PRT
<213> ORGANISM: Homo sapiens

<400> SEQUENCE: 6

```
Met Lys Val Leu Val Thr Gly Phe Glu Pro Phe Gly Gly Asp Lys Ile
1               5                   10                  15

Asn Pro Ser Trp Glu Ala Val Lys Gln Leu Asp Gly Val Arg Glu Ile
            20                  25                  30

Gly Gly Ala Thr Ile Val Gly Arg Glu Leu Pro Thr Ser Phe Lys Lys
        35                  40                  45

Ala Ala Glu Val Leu Lys Lys Ala Ile Ala Glu Ile Lys Pro Asp Ile
    50                  55                  60

Val Ile Ala Ile Gly Leu Ala Pro Gly Arg Ser Ala Ile Thr Val Glu
65                  70                  75                  80

Arg Val Ala Ile Asn Ile Asp Asp Ala Gly Arg Tyr Gly Ile Pro Asp
                85                  90                  95

Asn Glu Gly Glu Gln Pro Ile Asp Glu Pro Ile Val Pro Asp Gly Pro
            100                 105                 110

Ala Ala Tyr Phe Ala Thr Leu Pro Val Lys Ala Met Val Lys Ala Met
        115                 120                 125

Arg Glu Ala Gly Ile Pro Ala Ala Val Ser Asn Thr Ala Gly Thr Phe
    130                 135                 140
```

-continued

```
Val Cys Asn His Val Met Tyr Leu Leu Leu His His Ser Ala Lys Lys
145                 150                 155                 160

Gly Pro Pro Val Arg Ala Gly Phe Ile His Val Pro Tyr Leu Pro Glu
                165                 170                 175

Gln Val Val Asp Lys Pro Asn Thr Gly Gly Lys Val Val Pro Ser Met
            180                 185                 190

Ser Leu Asp Thr Glu Val Ala Gly Val Thr Ala Ala Ile Glu Ala Ala
        195                 200                 205

Leu Asp Tyr Asp
    210


<210> SEQ ID NO 7
<211> LENGTH: 2239
<212> TYPE: DNA
<213> ORGANISM: Homo sapiens

<400> SEQUENCE: 7

agtcgcaaca gaagcaggtc cgaggcacag cccgatcccg ccatggagca gccgaggaag      60

gcggtggtag tgacgggatt tggccctttt ggggaacaca ccgtgaacgc cagttggatt     120

gcagttcagg agctagaaaa gctaggcctt ggcgacagcg tggacctgca tgtgtacgag     180

attccggttg agtaccaaac agtccagaga ctcatccccg ccctgtggga gaagcacagt     240

ccacagctgg tggtgcatgt gggggtgtca ggcatggcga ccacagtcac actggagaaa     300

tgtggacaca acaagggcta caaggggctg gacaactgcc gcttttgccc cggctcccag     360

tgctgcgtgg aggacgggcc tgaaagcatt gactccatca tcgacatgga tgctgtgtgc     420

aagcgagtca ccacgttggg cctggatgtg tcggtgacca tctcgcagga tgccggcaga     480

tatctctgcg actttaccta ctacacctct ttgtaccaga gtcacggtcg atcagccttc     540

gtccacgtgc ccccactggg gaagccgtac aacgcggacc agctgggcag ggcactgaga     600

gccatcattg aggagatgtt ggacctcctg gagcagtcag agggcaaaat caactattgc     660

cacaaacact gagggacgct caggtctcct aagacctcat cctgctgggg accccacgag     720

gggacatcca ccctctgggg tgtggccagg aaaagacaag ctcttcagct tggggatccg     780

atctggaaga gagattctga tctgcccacc tcctcttcct tcttctctac aaaagctccg     840

gttgattcga gggaagtggt gaaaattttt ttttctccca ttttcctccc tgcatctggg     900

gacacagctg ccgtgaccag ggaggccagc ctgggaggtc cagatgccca gggagaatct     960

tggtctggtg aatccatgag ctgagatacc acggctgggg ccatatgttc acctgctttc    1020

ctgtccgttg gtgaaggaat ttcagaattc attttatatc caagactggc ttttaccaaa    1080

tttaaaagcc tctcaatgcg tcctcgacct tgaactgtgc tcaacagcct ggccctttct    1140

ggggccaccc tgggatatgg ctggctggct ggctggcttt ctttctttct ttctttcttt    1200

ctttctttct ttctttcttt ctttctttct ttcttgcttt ctttcttgct ttctttcttg    1260

ctttctttct ttcttgcttt ctttcttctc tctctctctt tttttttttt ttaaatagtg    1320

ctagtttggg cacagagtaa tttatattcc ctttggttaa aatgcaggct ttttagccaa    1380

caacaaaagt gttttccccc cacccccact cgcccaccag ggtgatgcca cttttgcctc    1440

ctgccctgaa aattggactt aagatgccat gtcttggctg ggattacagg catgagccac    1500

tgcacccagc ccagttcttt cttaaaacag ctgagagttt tgttttcttc agcgttcacc    1560

ttccttgtct ccagttccga tgctggcagt ggttcctacc tctgttgggt ttctagatag    1620

tttgggaacg gggttgatgg gtttctgtga aacacatttt ccaagtcttg ggctttctct    1680
```

-continued

```
ggaggggaag gtggatgctg gcgggtgact tgcagtgggc gcctggcagt gggtgtggac   1740

tgtaactgac aggtggaaat gagtaggggc actattgttc cctccatgcc agcttttttt   1800

ttgctggaaa tgccccctcc acacccctgg tagctctgtg tcctgagaaa tccagagtgt   1860

gggagacatc actgcatctg tccccccagc ttctgtgaag ggaagctgtg gcctcttttg   1920

aatgtgggga acaactgaag actcaggggt cacccagagg tctggtggaa agcaacttca   1980

ggtttcatct tgctctattc ctcaaaggtc tggtctgtgg gcctctgagg agaaaacagg   2040

tctagccaag acagggacaa aatggggaag gggtgtgcc aggcctgaac tgagctaagc   2100

acctgccccg ggctccacac ttccatcttt cttttgtctt catttcacct ctgtgtttaa   2160

agcactgtgt gacatagctc cttagagata taacctattg tctgctcatt gtcaaaaaaa   2220

aaaaaaaaaa aaaaaaaaa                                                2239
```